United States Patent
Merrill, Jr.

(10) Patent No.: US 10,317,333 B2
(45) Date of Patent: Jun. 11, 2019

(54) CENTRIFUGE MEMS STICTION TEST SYSTEM AND METHOD

(71) Applicant: MCube Inc., San Jose, CA (US)

(72) Inventor: Raymond Merrill, Jr., San Ramon, CA (US)

(73) Assignee: MCube Inc., San Jose, CA (US)

( * ) Notice: Subject to any disclaimer, the term of this patent is extended or adjusted under 35 U.S.C. 154(b) by 508 days.

(21) Appl. No.: 14/289,494

(22) Filed: May 28, 2014

(65) Prior Publication Data

US 2014/0352403 A1    Dec. 4, 2014

Related U.S. Application Data

(60) Provisional application No. 61/829,034, filed on May 30, 2013.

(51) Int. Cl.
  *G01N 19/02* (2006.01)
  *G01M 99/00* (2011.01)
  *B81C 99/00* (2010.01)

(52) U.S. Cl.
  CPC ........... *G01N 19/02* (2013.01); *B81C 99/005* (2013.01); *G01M 99/004* (2013.01); *G01N 2203/0037* (2013.01)

(58) Field of Classification Search
  CPC .............. B81C 99/0035; B81C 99/004; B81C 99/0045; B81C 99/005; G01N 19/02; G01N 2203/0031; G01M 99/004
  USPC .................................................. 73/865.3, 9
  See application file for complete search history.

(56) References Cited

U.S. PATENT DOCUMENTS

| 5,389,182 A | 2/1995 | Mignardi et al. |
| 6,445,203 B1 | 9/2002 | Yamashita et al. |
| 8,637,943 B1 | 1/2014 | Yang |
| 9,651,473 B2 | 5/2017 | Merrill et al. |
| 9,758,374 B2 | 9/2017 | Merrill et al. |

(Continued)

FOREIGN PATENT DOCUMENTS

| CN | 104069955 A | 10/2014 |
| TW | 201500115 | 1/2015 |

OTHER PUBLICATIONS

Rajesh et al., "An RF based Centrifuge Calibration for MEMS Accelerometer Testing", published Dec. 20, 2010.*

(Continued)

*Primary Examiner* — Lisa M Caputo
*Assistant Examiner* — Irving A Campbell
(74) *Attorney, Agent, or Firm* — Richard T. Ogawa; Ogawa P.C.

(57) ABSTRACT

A system for testing a device under a high gravitational force including a centrifuge with a rotating member and method of operation thereof. An operating power can be applied to a device, which can be coupled to the rotating member. The system can include a rotational control that can be coupled to the centrifuge. This rotational control can be configured to rotate the rotating member in response to a controlled number of revolutions per time period. The system can also include an analysis device for monitoring one or more signals from the device with respect to the controlled number of revolutions per time period. The analysis device can be configured to determine a stiction force associated with the DUT (Device Under Test) in response to the time-varying gravitational forces and to the one or more signals from the DUTs.

21 Claims, 10 Drawing Sheets

(56) References Cited

U.S. PATENT DOCUMENTS

| | | |
|---|---|---|
| 2009/0095095 A1 | 4/2009 | Hayashi |
| 2011/0156734 A1 | 6/2011 | Berry et al. |
| 2011/0260734 A1 | 10/2011 | Liao et al. |
| 2012/0304926 A1 | 12/2012 | Boguslavskiy et al. |
| 2014/0290331 A1* | 10/2014 | Merrill, Jr. ............. G01N 19/02 73/9 |
| 2014/0352403 A1 | 12/2014 | Merrill |
| 2015/0284245 A1 | 10/2015 | Merrill |

OTHER PUBLICATIONS

Acar, Cenk and Andrei M. Shkel, "Experimental evaluation and comparative analysis of commercial variable-capacitance MEMS acelerometers", published May 28, 2003.*
Walraven, "Failure Mechanisms in MEMS", published in 2003.*
Mastrangelo, C.H., Suppression of Stiction in MEMS, Mat. Res. Soc. Symp. Proc. vol. 605, 2000, pp. 105-116.*
Jouan KR4i Instruction Manual, Thermo Scientific, 2008.*
Non-Final Office Action received in U.S. Appl. No. 14/267,864, dated Jan. 12, 2017. 18 pages.
Restriction Requirement received in U.S. Appl. No. 14/267,864, dated Oct. 19, 2016, 7 pages.

* cited by examiner

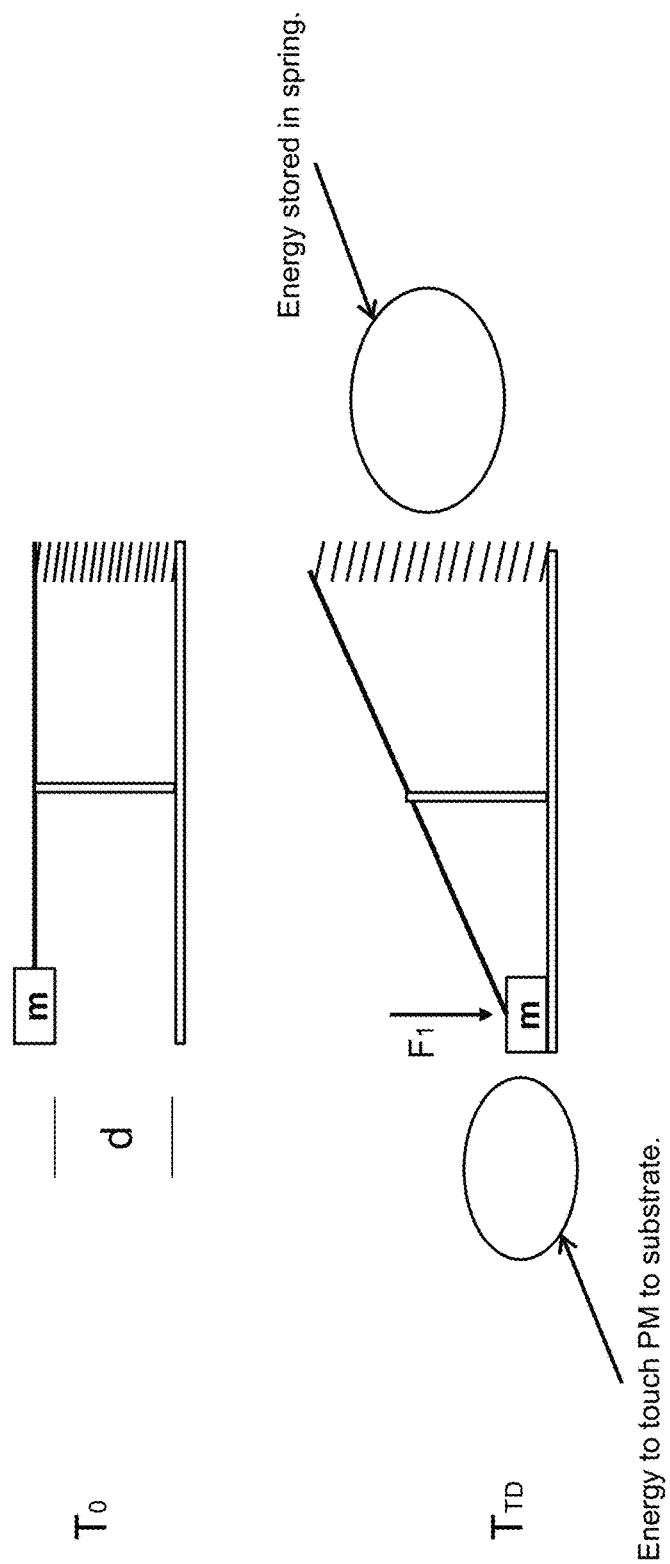

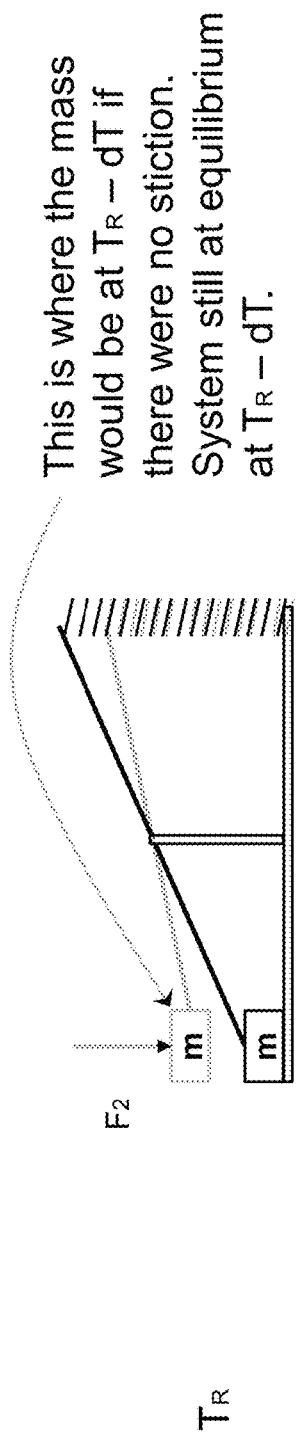

This is where the mass would be at $T_R - dT$ if there were no stiction. System still at equilibrium at $T_R - dT$.

- The touchdown energy IS the restoring force. It is the energy stored in the spring.

Stiction energy equals touchdown energy minus release energy.

Taking the ratio of stiction acceleration ($a_1 - a_2$) and touchdown acceleration ($a_1$) is equivalent to the ratio of energies.

FIG. 7

- Restoring Energy Variability Estimate

The restoring energy is the energy stored in the spring. It is reduced by factor $v_r$ due to particle.

- Stiction Energy Variability Estimate

The stiction energy is increased by factor $v_s$ due to process variability.

FIG. 9

- Final calculation to determine the stiction margin limit.

$$\frac{E_{(stiction)}}{E_{TD}} < \frac{v_r}{v_s}$$

FIG. 10

CENTRIFUGE MEMS STICTION TEST SYSTEM AND METHOD

CROSS-REFERENCES TO RELATED APPLICATIONS

The present application claims priority to and incorporates by reference, for all purposes, the following provisional patent application: U.S. Provisional App. No. 61/829,034, filed May 30, 2013. The present application also incorporates by reference, for all purposes, the following pending patent applications: U.S. patent application Ser. No. 14/222,575, filed Mar. 21, 2014, and U.S. patent application Ser. No. 14/267,864, filed May 1, 2014.

BACKGROUND OF THE INVENTION

The present invention is directed to MEMS (Micro-Electro-Mechanical-Systems). More specifically, embodiments of the invention provide methods and systems for testing MEMS devices and components, including inertial sensors and the like.

Research and development in integrated microelectronics have continued to produce astounding progress in CMOS and MEMS. CMOS technology has become the predominant fabrication technology for integrated circuits (IC). MEMS, however, continues to rely upon conventional process technologies. In layman's terms, microelectronic ICs are the "brains" of an integrated device which provides decision-making capabilities, whereas MEMS are the "eyes" and "arms" that provide the ability to sense and control the environment. Some examples of the widespread application of these technologies are the switches in radio frequency (RF) antenna systems, such as those in the iPhone™ device by Apple, Inc. of Cupertino, Calif., and the Blackberry™ phone by Research In Motion Limited of Waterloo, Ontario, Canada, and accelerometers in sensor-equipped game devices, such as those in the Wii™ controller manufactured by Nintendo Company Limited of Japan. Though they are not always easily identifiable, these technologies are becoming ever more prevalent in society every day.

Beyond consumer electronics, use of IC and MEMS has limitless applications through modular measurement devices such as accelerometers, gyroscopes, actuators, and sensors. In conventional vehicles, accelerometers and gyroscopes are used to deploy airbags and trigger dynamic stability control functions, respectively. MEMS gyroscopes can also be used for image stabilization systems in video and still cameras, and automatic steering systems in airplanes and torpedoes. Biological MEMS (Bio-MEMS) implement biosensors and chemical sensors for Lab-On-Chip applications, which integrate one or more laboratory functions on a single millimeter-sized chip only. Other applications include Internet and telephone networks, security and financial applications, and health care and medical systems. As described previously, ICs and MEMS can be used to practically engage in various type of environmental interaction.

Although highly successful, ICs and in particular MEMS still have limitations. Similar to IC development, MEMS development, which focuses on increasing performance, reducing size, and decreasing cost, continues to be challenging. Additionally, applications of MEMS often require increasingly complex microsystems that desire greater computational power. Unfortunately, such applications generally do not exist. These and other limitations of conventional MEMS and ICs may be further described throughout the present specification and more particularly below.

From the above, it is seen that techniques for improving the manufacture of integrated circuit devices and MEMS are highly desired.

BRIEF SUMMARY OF THE INVENTION

The present invention is directed to MEMS (Micro-Electro-Mechanical-Systems). More specifically, embodiments of the invention provide methods and systems for testing MEMS devices and components. Merely by way of example, the MEMS device can include at least an accelerometer, a gyroscope, a magnetic sensor, a pressure sensor, a microphone, a humidity sensor, a temperature sensor, a chemical sensor, a biosensor, an inertial sensor, and others. But it will be recognized that the invention has a much broader range of applicability.

Embodiments of the present invention can include a system and method of testing MEMS devices using the system. In an embodiment, the present invention provides a system for testing a device under a high gravitational force including a centrifuge with a rotating member. An operating power can be applied to a device, which can be coupled to the rotating member. The system can include a rotational control that can be coupled to the centrifuge. This rotational control can be configured to rotate the rotating member in response to a controlled number of revolutions per time period. The system can also include an analysis device for monitoring one or more signals from the device with respect to the controlled number of revolutions per time period. Those of ordinary skill in the art will recognize other variations, modifications, and alternatives.

In a specific embodiment, the rotating member can additional include a power source coupled to the device. This power source can be a battery, a capacitor, or the like, and can be configured to provide the operating power to the device. The rotating member can also include a communication source coupled to the device. This communication source can be configured to provide signals from the device to the analysis device. The communication source can include sources such as Wi-Fi, wireless, optical, Bluetooth, near field communications, microwave, laser, or the like and combinations thereof. Furthermore, the analysis device can include a communication receiver configured to receive the signals from this communications source.

In a specific embodiment, the device comprises a MEMS-based accelerometer. The controlled revolutions per time period can include a controlled time varying number of revolutions per time period. In this case, the analysis device can be configured to determine time-varying gravitational forces applied to the device in response to the controlled time varying number of revolutions per time period. The analysis device can also be configured to determine a stiction force associated with the MEMS-based accelerometer in response to the time-varying gravitational forces and to the one or more signals from the MEMS-based accelerometer. In a specific embodiment, these one or more signals can be associated with a restoring force associated with the MEMS-based accelerometer.

In an embodiment, the present invention provides a method for determining defective devices under a high gravitational force. This method can include coupling a device to a rotating member of a centrifuge and applying an operating power to the device. The rotating member of the centrifuge can have a controlled rotational speed while the device has the operating power applied thereto. This rotational speed can be associated with a gravitational force. Afterwards, one or more signals from the device can be received in a computing device while the device has the operating power applied thereto and while subject to the gravitational force. Using the computing device, the device can be determined to be defective or not in response to the one or more signals and to the gravitational force.

In a specific embodiment, the method can include coupling a power source coupled to the rotating member and to the device to thereby provide the operating power to the device. This power source can be selected from a battery, a capacitor, or the like.

In specific embodiment, the method can also include applying a trim factor to the device while the device has the operating power applied thereto, and outputting, from the device, the one or more signals in response to the trim factor while the device has the operating power applied thereto and while subject to the gravitational force. Also, the one or more signals can be output from a communications source coupled to the centrifuge. These one or more signals can be output from a communication mechanism selected from Wi-Fi, wireless, optical, Bluetooth, near field communications, microwave, laser, or the like.

In a specific embodiment, the device can include a MEMS-based accelerometer and the method step of controlling the rotational speed can include varying the rotational speed of the rotating member in time. A stiction source associated with the accelerometer in response to the one or more signals and to the rotational speed can be determined in the computing device. Furthermore, the one or more signals can be associated with a restoring force associated with the MEMS-based accelerometer.

Other embodiments of the present invention can be directed towards testing a variety of MEMS-based devices having a proof mass.

Various additional objects, features and advantages of the present invention can be more fully appreciated with reference to the detailed description and accompanying drawings that follow.

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which:

FIG. 6 is simplified diagram illustrating a method of analyzing a centrifuge measurement system according to an embodiment of the present invention;

FIG. 7 is simplified diagram illustrating conservation of energy of a DUT according to an embodiment of the present invention;

FIGS. 9 and 10 are simplified representations of calculations for energy variability estimates and stiction margins according to an embodiment of the present invention.

DETAILED DESCRIPTION OF THE INVENTION

The present invention is directed to MEMS (Micro-Electro-Mechanical-Systems). More specifically, embodiments of the invention provide methods and systems for testing MEMS devices and components. Merely by way of example, the MEMS device can include at least an accelerometer, a gyroscope, a magnetic sensor, a pressure sensor, a microphone, a humidity sensor, a temperature sensor, a chemical sensor, a biosensor, an inertial sensor, and others. But it will be recognized that the invention has a much broader range of applicability.

Embodiments of the present invention provide a system and a method for stimulating MEMS contact in a controlled way so as to measure stiction related effects in MEMS devices. This method can be applied to MEMS devices in any phase of development, from the wafer to a fully encapsulated device.

In many MEMS devices, silicon structures are either designed to move, or move as a secondary effect, as the result of a given acceleration, and these structures come into contact with another surface as the end of travel is reached. A problem with typical methods of stimulating a MEMS device is that reaching the point of contact involves shocking the devices mechanically, which is far more costly and time consuming. Also, the shock dynamics of such testing can confound measurements of stiction energy and the like.

In an embodiment, the present invention provides a centrifuge stiction measurement system including a tachometer and method of operation thereof. The centrifuge stiction measurement system can be computer operated and/or controlled manually from a front panel. Many benefits are provided through one or more embodiments of the present invention. This measurement system can be used to provide a continuous, non-destructive way to expose MEMS devices or parts to g-forces high enough to cause contact between moving parts. Using this method provides an easier, quicker, cheaper, and more deterministic means for stiction testing compared to shock testing.

Furthermore, if any given MEMS part remains stuck after the g-force is removed, then the die can then be detected by chip probe and removed from the product population.

Figure 1:
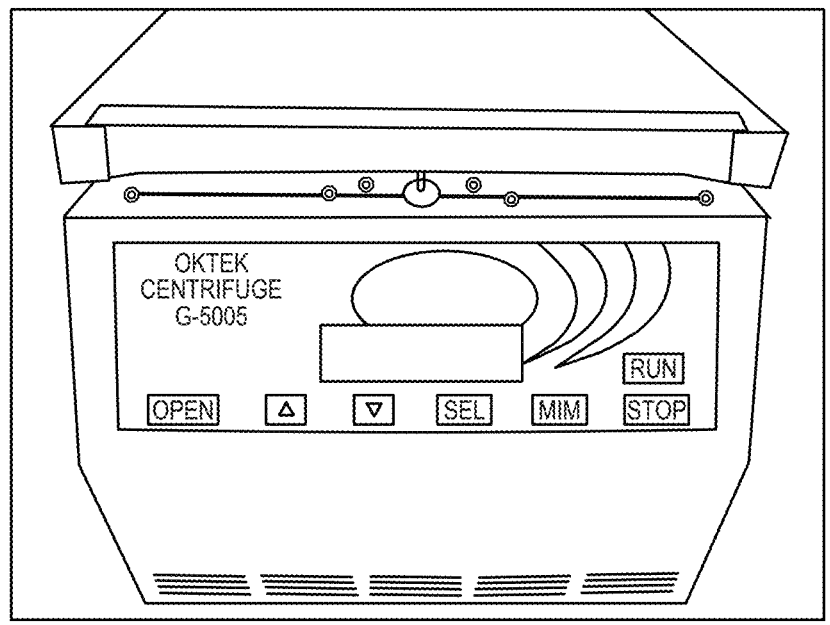
FIG. 1 is a picture of a conventional centrifuge.

FIG. 1 is a picture of a conventional centrifuge. This centrifuge is an OKTEK model G-5005. Embodiments of the present invention can include such a centrifuge with custom hardware designed to provide a unique platform for exposing MEMS devices and parts to a rotational centrifugal force (RCF). Other off-the-shelf centrifuge models and the like can be used in the centrifuge systems as described herein. These systems can be designed for ease of use and safety.

Figure 2:
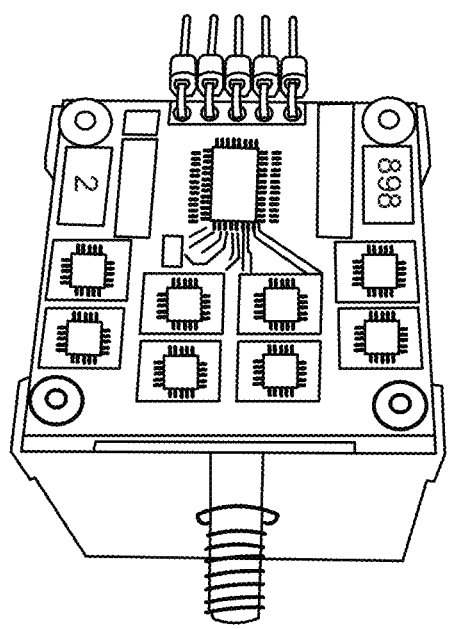
FIG. 2 is a picture of a device under test (DUT) system according to an embodiment of the present invention.

FIG. 2 is a picture of a custom 8 DUT (Device Under Test) centrifuge board mounted to a multi-axis test block. This DUT test board can be configured for eight devices (shown on the circuit board), which can be MEMS devices, MEMS packaged parts, or the like.

Figure 3:
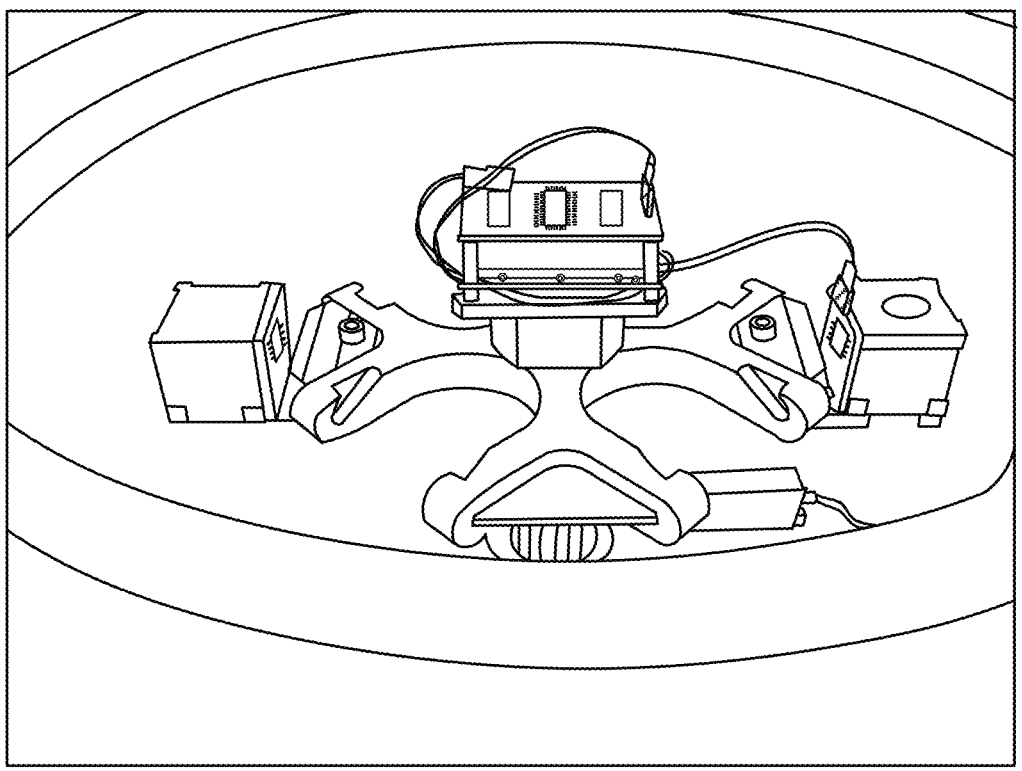
FIG. 3 is a picture of centrifuge measurement system with custom modifications according to an embodiment of the present invention.

FIG. 3 is a picture of centrifuge measurement system with custom modifications according to an embodiment of the present invention. As shown, a battery powered Bluetooth transceiver is mounted in the center of the hub. Two DUT boards are mounted on opposite ends. These DUT boards can be the custom 8 DUT centrifuge boards shown in FIG. 2. This configuration provides 16 DUT capability in a single run.

Figure 4:
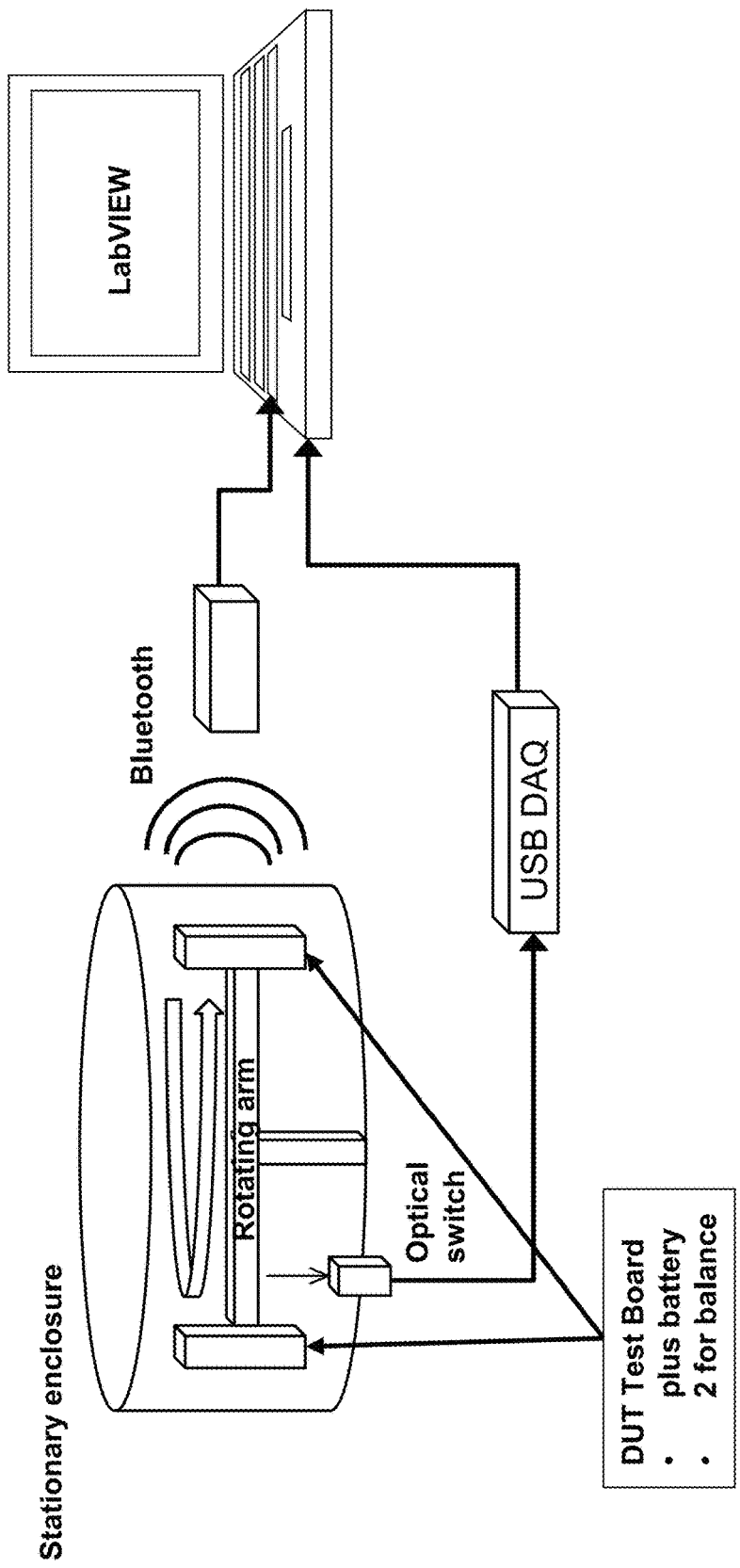
FIG. 4 is a simplified diagram illustrating a device under test (DUT) system or centrifuge measurement system according to an embodiment of the present invention.

FIG. 4 is a simplified diagram illustrating a device under test (DUT) system or centrifuge measurement system according to an embodiment of the present invention. The DUT may be a wafer, a die, a packaged chip, a powered packaged chip, or the like. As shown, a stationary enclosure containing a rotating member or arm can be coupled to a computing device. The stationary enclosure can be a base centrifuge device or system, such as the OKTEK model G-5005 shown in FIG. 1. Similar to FIG. 3, DUT test boards and batteries can be coupled to the ends of the rotating arms. The gravitational force one the DUT can be expressed by the following equation.

$$G = N^2 * R * 1.1182e\text{-}5$$

N is RPM
R is Radius (cm)
G is g's (Earth)

In a specific embodiment, the rotating member can additional include a power source coupled to the device. This power source can be a battery, a capacitor, or the like, and can be configured to provide the operating power to the device. The rotating member can also include a communication source coupled to the device. This communication source can be configured to provide signals from the device to the analysis device. The communication source can include sources such as Wi-Fi, wireless, optical, Bluetooth, near field communications, microwave, laser, or the like and combinations thereof. Furthermore, the analysis device can include a communication receiver configured to receive the signals from this communications source.

In a specific embodiment, the device comprises a MEMS-based accelerometer. The controlled revolutions per time period can include a controlled time varying number of revolutions per time period. In this case, the analysis device can be configured to determine time-varying gravitational forces applied to the device in response to the controlled time varying number of revolutions per time period. The analysis device can also be configured to determine a stiction force associated with the MEMS-based accelerometer in response to the time-varying gravitational forces and to the one or more signals from the MEMS-based accelerometer. In a specific embodiment, these one or more signals can be associated with a restoring force associated with the MEMS-based accelerometer.

In an embodiment, the centrifuge measurement system can be configured with several custom modifications to facilitate the testing of MEMS devices, packaged MEMS parts, and the like. The rotating arm can be controlled via an optical switch that is electrically coupled to a USB (Universal Serial Bus) DAQ (Data Acquisition) module. This USB DAQ module can be coupled to a computing device, such as a desktop computer, a tablet, a mobile phone, or the like. Also, a Bluetooth transceiver can be provided within the stationary enclosure and be configured to transmit data from the DUT test boards (as shown in FIG. 2). The data from Bluetooth transceiver can be processed using a variety of software measurement tools, such as LabVIEW and the like.

Figure 5:
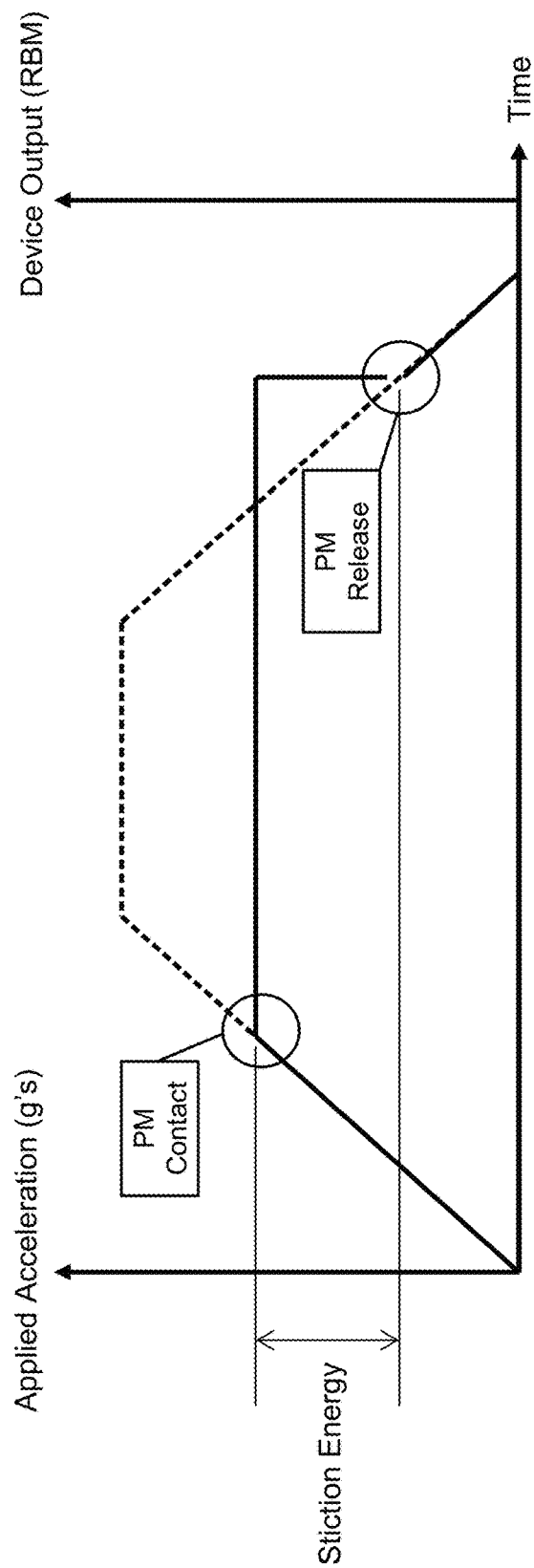
FIG. 5 is a simplified graph illustrating a method of operating a centrifuge measurement system according to an embodiment of the present invention.

FIG. 5 is a simplified graph illustrating a method of operating a centrifuge measurement system according to an embodiment of the present invention. More specifically, this graph shows Applied Acceleration (g's) over time and the relationship between this acceleration profile and stiction energy found in the DUT according to the Device Output (RBM) over time. Two key points are noted where the MEMS Proof Mass (PM) makes contact with the MEMS stop structures, and when the PM is released.

In an embodiment, the present invention provides a method for determining defective devices under a high gravitational force. This method can include coupling a device to a rotating member of a centrifuge and applying an operating power to the device. The rotating member of the centrifuge can have a controlled rotational speed while the device has the operating power applied thereto. This rotational speed can be associated with a gravitational force. Afterwards, one or more signals from the device can be received in a computing device while the device has the operating power applied thereto and while subject to the gravitational force. Using the computing device, the device can be determined to be defective or not in response to the one or more signals and to the gravitational force.

In a specific embodiment, the method can include coupling a power source coupled to the rotating member and to the device to thereby provide the operating power to the device. This power source can be selected from a battery, a capacitor, or the like.

In specific embodiment, the method can also include applying a trim factor to the device while the device has the operating power applied thereto, and outputting, from the device, the one or more signals in response to the trim factor while the device has the operating power applied thereto and while subject to the gravitational force. Also, the one or more signals can be output from a communications source coupled to the centrifuge. These one or more signals can be output from a communication mechanism selected from Wi-Fi, wireless, optical, Bluetooth, near field communications, microwave, laser, or the like.

In a specific embodiment, the device can include a MEMS-based accelerometer and the method step of controlling the rotational speed can include varying the rotational speed of the rotating member in time. A stiction source associated with the accelerometer in response to the one or more signals and to the rotational speed can be determined in the computing device. Furthermore, the one or more signals can be associated with a restoring force associated with the MEMS-based accelerometer.

FIG. 6 is simplified diagram illustrating a method of analyzing a centrifuge measurement system according to an embodiment of the present invention. This figure provides energy equations used for interpreting data during a centrifuge test of one or more devices. As noted, there are three key moments during the test: $T_0$ at the beginning of the test, $T_{TD}$ at time of touchdown, and $T_R$ at time of release. At $T_0$, the centrifuge is operating at 0 RPM, and thus, $a_z=0$ g. At $T_{TD}$, there is an acceleration ramp up to a first acceleration where $a_z=a_1$. At $T_R$, there is an acceleration ramp down to a second acceleration where $a_z=a_2$. As shown, the DUT is a device with a proof mass (PM) acting as a spring. The equations or the energy to touch the PM to the substrate surface $E_{Td}=F \times d$ and the energy stored in a spring $E_s=(\frac{1}{2})K \times d^2$ are provided. Here, $E_{Td}=E_s$.

FIG. 7 is simplified diagram illustrating conservation of energy of a DUT according to an embodiment of the present invention. Here, it is shown that the touchdown energy is the restoring force, which is the energy stored in the spring. The device shown represents the position of the proof mass if there is no stiction. With stiction, the stiction energy equals the touchdown energy minus the release energy.

$$E_{(stiction)} = E_{T_D} - E_R = (m \cdot a_1 \cdot d) - (m \cdot a_2 \cdot d)$$

$$E_{(stiction)} = (a_1 - a_2) \cdot m \cdot d$$

Taking a ratio of the stiction acceleration (a1-a2) and touchdown acceleration (a1) is equivalent to the ratio of energies.

$$\frac{(a_1 - a_2)}{a_1} = \frac{\frac{E_{(stiction)}}{(m \cdot d)}}{\frac{E_{T_D}}{(m \cdot d)}} = \frac{E_{(stiction)}}{E_{T_D}} = 1 - \frac{E_R}{E_{T_D}}$$

Where:
Er=Release Energy
$E_{TD}$=Touchdown Energy
E(stiction)=Stiction Energy.

The intrinsic stiction energy is defined as the stiction energy resulting from pure surface physics (i.e. Van der Waals forces). Other factors add to the intrinsic stiction energy to form the total stiction energy. Such factors may include contaminants in the form of films (organics), contact surface finishes/topology, particles, surface hardness (shock can change topology if soft), and the like. These other factors can vary considerably with fabrication process variations and many things can affect the stiction recovery potential of a MEMS device (shown in FIG. 8). All of these factors show why a stiction margin is needed.

Figure 8:
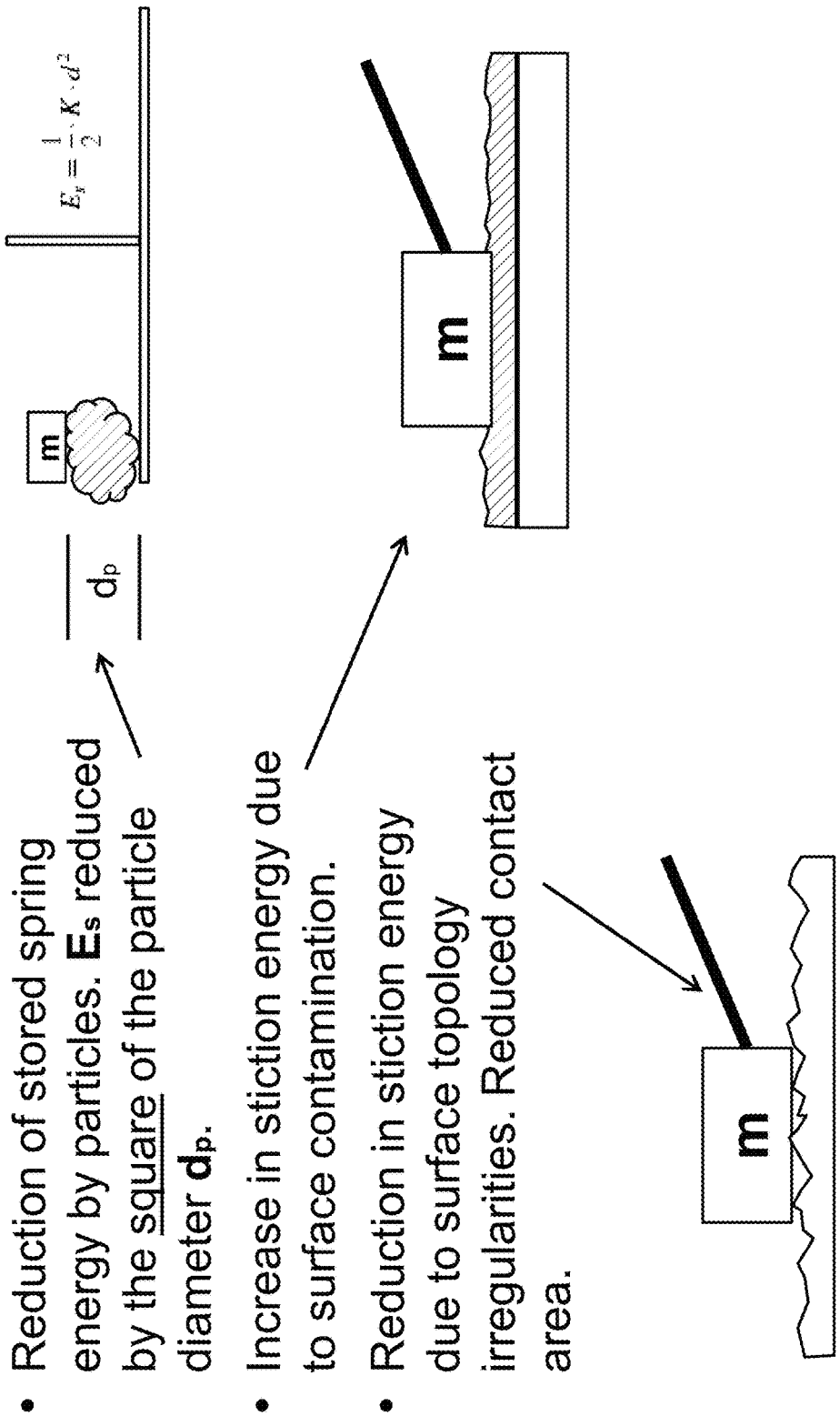
FIG. 8 is simplified diagram illustrating stiction recovery considerations for a DUT according to an embodiment of the present invention.

FIG. 8 is simplified diagram illustrating stiction recovery considerations for a DUT according to an embodiment of the present invention. The top figure shows the effect that particles have on the reduction of stored spring energy. $E_s$ is reduced by the square of the particle diameter $d_p$. The middle figure shows the increase in stiction energy due to surface contamination. The bottom figure shows the reduction in stiction energy due to surface topology irregularities, which causes reduced contact area.

If there were no variability in the stiction energies or the release energy, it would be enough to set a stiction limit of $E_{(stiction)}/E_{TD} < 1.0$. In other words, $E_{TD} > E_{(stiction)}$. However, due to the variability, it is necessary to have a margin between the release energy and touchdown energy to ensure parts in the field do not stick. To approximate the margin necessary to ensure release over all variability, we can use SEM particle size data and empirical stiction data from the centrifuge test methods and systems described herein.

FIGS. 9 and 10 are simplified representations of calculations for energy variability estimates and stiction margins according to an embodiment of the present invention. The restoring energy is the energy stored in the spring, and it is reduced by a factor of $v_r$ due to particle size. Here $v_r$ is a unitless fraction by which the restoring energy is reduced.

$$E_s' = E_s \cdot v_r$$

In a specific embodiment, this factor is estimated from design and SEM data for Metal Bump devices to be $v_r = (1 - (0.5/1.6)^2 = 0.473$. Vr can be calculated as follows.

$$\frac{1}{2} \cdot K \cdot (d - d_p)^2 = \frac{1}{2} \cdot K \cdot d^2 \cdot v_r \therefore v_r = \left(1 - \frac{d_p}{d}\right)^2$$

where K is the spring constant, d is the distance to the substrate, and dp is the diameter of the particle. Also, the stiction energy is increased by a factor of $v_s$ due to process variability. Here $v_s$ is a unitless fraction by which the restoring energy is reduced. The stiction energy can be increased by a factor Vr due to process variability.

$$E_{(stiction)}' = E_{(stiction)} \cdot v_s$$

In a specific embodiment, this factor is estimated from empirical variability data from centrifuge tests to be $v_s \approx 80/20 = 4$. In this example, 80 and 20 represent a higher limit of the stiction energy and a lower limit of stiction energy due to process variation. Using these factors (shown in FIG. 10), a final stiction margin can be determined as $E_{(stiction)}/E_{TD} = v_r/v_s = 14\%$. Here, to insure no stiction, we need, $$E_s' > E_{(stiction)}'$$

Substituting:

$$v_r \cdot E_s > v_s \cdot E_{(stiction)}$$

From above, $$E_s = E_{T_D}$$

Substituting and rearranging, we obtain that following.

$$\frac{E_{(stiction)}}{E_{TD}} < \frac{v_r}{v_s}$$

Of course, there can be other variations, modifications, and alternatives.

Figure 11:
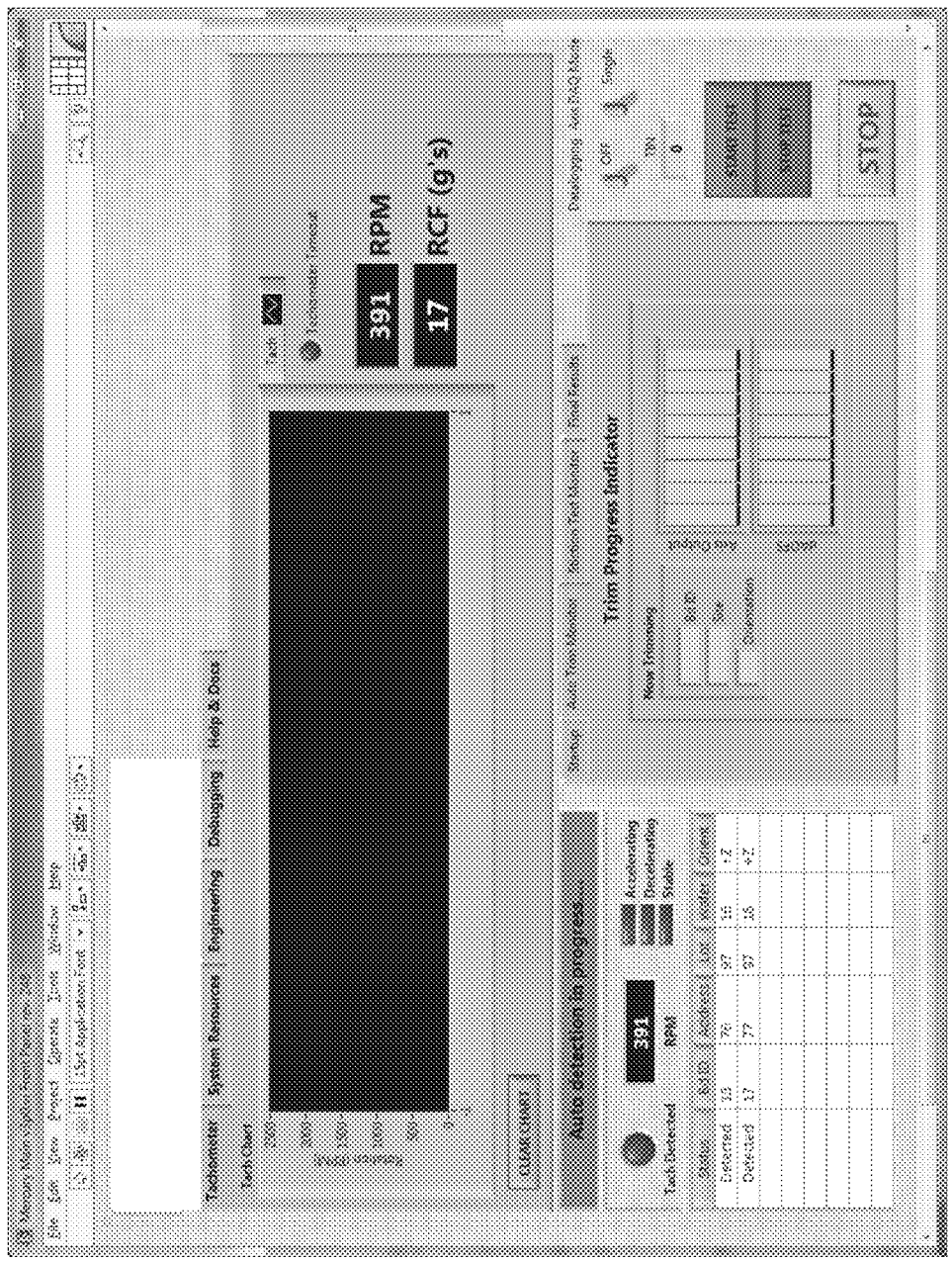
FIG. 11 is simplified diagram illustrating a graphical user interface of an analysis device according to an embodiment of the present invention.

FIG. 11 is simplified diagram illustrating a graphical user interface of an analysis device according to an embodiment of the present invention. Data from the DUTs can be recorded and displayed on a screen to allow a user to easily determine the quality of these devices.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A system for testing a device under a centrifugal force, comprising:
    a centrifuge comprising a rotating member;
    the device coupled to the rotating member, wherein the device has an operating power applied thereto;
    a rotational control coupled to the centrifuge, wherein the rotational control is configured to rotate the rotating member in response to a controlled number of revolutions per time period;
    an analysis device for monitoring one or more signals from the device with respect to the controlled number of revolutions per time period;
    wherein the system is further configured to:
    determine a stiction energy and a restoring energy in the device by varying a rotating speed of the centrifuge, wherein a profile of the rotating speed includes:
        a first time period in which the rotating speed is increased to reach a first speed at which stiction takes place;
        a second time period during which the rotation speed is maintained at the first speed; and a third time period in which the rotating speed is decreased to cause the stiction to be released at a second speed;

determine a stiction energy variability factor $V_s$, which is a unitless fraction by which the stiction energy is increased due to process variability and is estimated from empirical process variability data;

determine a restoring energy variability factor $V_r$, which is a unitless fraction by which the restoring energy is reduced due to particles and is estimated with metal bump device tests using metal bumps representing particles having different diameters;

calculate a fraction vr/vs, and set (vr/vs)×(the restoring energy) as a stiction margin limit; and determine the device to be defective if the stiction energy is greater than (vr/vs)×(the restoring energy).

2. The system of claim 1 wherein the rotating member further comprises a power source coupled to the device, wherein the power source is configured to provide the operating power to the device.

3. The system of claim 2 wherein the power source is selected from a group consisting of a battery and a capacitor.

4. The system of claim 1 wherein the rotating member further comprises a communication source coupled to the device, wherein the communication source is configured to provide the one or more signals from the device to the analysis device.

5. The system of claim 4 wherein the communication source is provided by a technology selected from a group consisting of Wi-Fi, wireless, optical, Bluetooth, near field communications, microwave, and laser.

6. The system of claim 5 wherein the analysis device comprises a communications receiver configured to receive the one or more signals from the communications source.

7. The system of claim 1 wherein the device comprises a MEMS-based accelerometer.

8. The system of claim 7 wherein the controlled number of revolutions per time period comprises a controlled time-varying number of revolutions per time period.

9. The system of claim 8 wherein the analysis device is configured to determine time-varying gravitational forces applied to the device in response to the controlled time varying number of revolutions per time period, and wherein the analysis device is also configured to determine the stiction energy associated with the MEMS-based accelerometer in response to the time-varying gravitational forces and to the one or more signals.

10. The system of claim 9 wherein the one or more signals are associated with the restoring energy associated with the MEMS-based accelerometer.

11. The system of claim 1, wherein the centrifuge comprises a power supply.

12. A method for testing a MEMS ((Micro-Electro-Mechanical-Systems) device under a centrifugal force, comprising:

coupling the MEMS device to a rotating member of a centrifuge, wherein the MEMS device has an operating power applied thereto;

controlling a rotational speed of the rotating member of the centrifuge while the MEMS device has the operating power applied thereto, wherein the rotational speed is associated with a gravitational force thereafter;

receiving one or more signals from the MEMS device in a computing device, while the MEMS device has the operating power applied thereto;

determining a stiction energy and a restoring energy in the MEMS device by varying the rotating speed of the centrifuge, wherein a profile of the rotating speed includes:
 a first time period in which the rotating speed is increased to reach a first speed at which stiction takes place;
 a second time period during which the rotation speed is maintained at the first speed; and
 a third time period in which the rotating speed is decreased to cause the stiction to be released at a second speed;

determining a stiction energy variability factor $V_s$, which is a unitless fraction by which the stiction energy is increased due to process variability and is estimated from empirical variability data;

determining a restoring energy variability factor $V_r$, which is a unitless fraction by which the restoring energy is reduced due to particles and is estimated with metal bump device tests using metal bumps representing particles having different diameters; and calculating a fraction vr/vs, and setting (vr/vs)×(the restoring energy) as a stiction margin limit; and determining the device to be defective if the stiction energy is greater than (vr/vs)×(the restoring energy).

13. The method of claim 12 further comprising coupling a power source to the rotating member and to the MEMS device to thereby provide the operating power to the device.

14. The method of claim 13 wherein the power source is selected from a group consisting of a battery and a capacitor.

15. The method of claim 12 further comprising outputting the one or more signals from a communications source coupled to the centrifuge.

16. The method of claim 15 wherein the one or more signals are output from a communications mechanism selected from a group consisting of Wi-Fi, wireless, optical, Bluetooth, near field communications, microwave, and laser.

17. The method of claim 12 wherein the MEMS device comprises a MEMS-based accelerometer.

18. The method of claim 17 wherein controlling the rotational speed comprises varying the rotational speed of the rotating member in time.

19. The method of claim 17 further comprising:
 determining, in the computing device, the stiction energy associated with the MEMS-based accelerometer in response to the one or more signals and to the rotational speed.

20. The method of claim 17 wherein the one or more signals are associated with the restoring energy associated with the MEMS-based accelerometer.

21. The method of claim 12 further comprising determining that the MEMS device is defective if the determined stiction energy of the MEMS device is higher than the stiction margin limit.

* * * * *